(12) United States Patent
Holla et al.

(10) Patent No.: US 7,825,144 B2
(45) Date of Patent: Nov. 2, 2010

(54) METHOD FOR THE PRODUCTION OF OXAZOLES BY CONDENSING AROMATIC ALDEHYDES WITH α-KETOXIMES TO N-OXIDES AND THEN REACTING THE SAME WITH ACTIVATED ACID DERIVATIVES

(75) Inventors: Wolfgang Holla, Kelkheim (DE); Rolf-Ludwig Hoerlein, Frankfurt (DE); Berndt Kulitzscher, Steinmark (DE); Wolfgang Laux, Frankfurt (DE); Thomas Stuedemann, Kelkheim (DE); Christoph Tappertzhofen, Frankfurt (DE); Robert J. H. Scheffer, Ingelheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/509,853

(22) Filed: Jul. 27, 2009

(65) Prior Publication Data

US 2009/0286988 A1    Nov. 19, 2009

Related U.S. Application Data

(63) Continuation of application No. 11/928,117, filed on Oct. 30, 2007, now abandoned, which is a continuation of application No. 11/754,477, filed on May 29, 2007, now Pat. No. 7,544,809, which is a continuation of application No. PCT/EP2005/012800, filed on Dec. 1, 2005.

(30) Foreign Application Priority Data

Dec. 15, 2004   (DE) .................. 10 2004 060 227

(51) Int. Cl.
A61K 31/421 (2006.01)
C07D 263/30 (2006.01)
(52) U.S. Cl. .................. 514/374; 548/215; 548/235
(58) Field of Classification Search .................. 548/215, 548/235; 514/374
See application file for complete search history.

(56) References Cited

U.S. PATENT DOCUMENTS 5,036,079 A    7/1991  Clark et al.
7,544,809 B2 *  6/2009  Holla et al. .................. 548/235

FOREIGN PATENT DOCUMENTS

| WO | WO 02/16332 | 2/2002 |
|---|---|---|
| WO | WO 02/100403 | 12/2002 |
| WO | WO 2004/075815 | 9/2004 |
| WO | WO 2004/076426 | 9/2004 |

OTHER PUBLICATIONS

Bodendorf et al (1965): STN International HCAPLUS database, Columbus (OH), accession No. 1965: 431655.*
Palmer, D. C., et. al., Synthesis and Reactions of Oxazoles, The Chemistry of Heterocyclic Compounds, vol. 60, Oxazoles: Synthesis, Reactions, and Spectroscopy, Part A, (2003), pp. 1-390.

* cited by examiner

Primary Examiner—Golam M Shameem
(74) Attorney, Agent, or Firm—Jiang Lin

(57) ABSTRACT

The invention is related to a process for preparing compounds of the formula IV by means of conversion of aromatic aldehydes of the formula I using α-ketoximes of the formula II via N-oxides of the formula III to halomethyloxazoles of the formula IV,

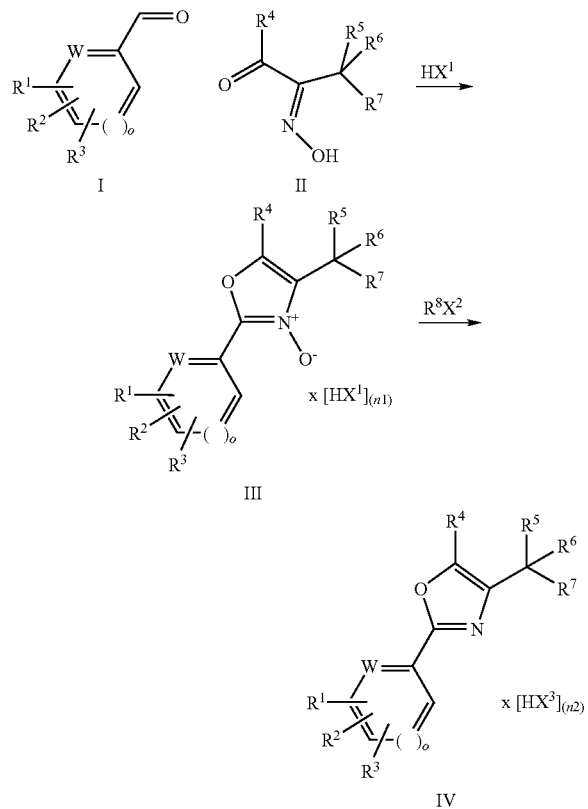

wherein $R^1$, $R^2$, $R^3$, $R^4$, $R^5$, $R^6$, $R^7$, $R^8$, $X^1$, $X^2$, $X^3$, o, n1 and n2 are as defined herein.

8 Claims, No Drawings

METHOD FOR THE PRODUCTION OF OXAZOLES BY CONDENSING AROMATIC ALDEHYDES WITH α-KETOXIMES TO N-OXIDES AND THEN REACTING THE SAME WITH ACTIVATED ACID DERIVATIVES

This application is a Continuation of application Ser. No. 11/928,117, filed Oct. 30, 2007, which is a Continuation of application Ser. No. 11/754,477, filed May 29, 2007, now issued as U.S. Pat. No. 7,544,809 on Jun. 9, 2009, which is a Continuation of International Application No. PCT/EP2005/012800, filed on Dec. 1, 2005, all of which are incorporated herein by reference in their entireties.

FIELD OF THE INVENTION

The invention relates to a process for preparing oxazoles by condensation of aldehydes with α-ketoximes to give N-oxides in the form of their salts or as free bases and subsequent reaction with activated acid derivatives to give oxazoles in the form of their salts or as free bases, in particular the condensation between aromatic aldehydes and α-ketoximes followed by the reaction of inorganic thionyl halides or organic sulfonyl halides to give chloromethyloxazoles.

BACKGROUND OF THE INVENTION

The invention allows the preparation of oxazoles in high yield and great purity. Oxazoles constitute valuable intermediates in the synthesis of pharmaceutically active substances, for example PPAR agonists. Appropriate examples of PPAR agonists are described, inter alia, in WO 03/020269, WO 2004/075815, WO 2004/076447, WO 2004/076428, WO 2004/076426, WO 2004/076427, DE 102004039533.0, DE 102004039532.2, DE 102004039509.8. The latter are medicaments which can have a positive influence both on lipid metabolism and on glucose metabolism.

The condensation of aromatic aldehydes with α-ketoximes to give N-oxides and the subsequent reaction with activated acid derivatives to give oxazoles is known per se. For the conversion of the N-oxides to the oxazoles, the literature describes the reagents phosphorus (III) chloride ($PCl_3$) and phosphorus oxychloride ($POCl_3$) and, in one variant, acetic anhydride (($CH_3COO)_2O$) (Y. Goto, M. Yamazaki, M. Hamana, Chem Pharm Bull. 19 (1971) 2050, and literature cited there). These reagents are not widely applicable and often lead to no products or to highly contaminated products which can only be obtained in sufficient purity with low yields in a costly and inconvenient manner, for example by chromatographic processes.

The reaction conditions described require the isolation of the N-oxides. For N-oxides with exothermic decomposition potential, this constitutes a considerable safety risk and prevents the process from being practiced on the industrial scale.

It has now been found that, surprisingly, the transformation of the N-oxides to the halomethyloxazoles proceeds unexpectedly smoothly with high yield and great purity with inorganic thionyl halides or organic sulfonyl halides.

Although it was unexpected on the basis of the remarks in the literature, halomethyloxazoles in some cases precipitate cleanly directly out of the reaction mixture in the form of the free base or as salts.

Unexpectedly, for N-oxides with exothermic decomposition potential, it has been possible to achieve both safe preparation in dilute solution and the further direct reaction of the solution to give the halomethyloxazoles.

SUMMARY OF THE INVENTION

The invention thus relates to a process for preparing compounds of the formula IV by means of conversion of aromatic aldehydes of the formula I using α-ketoximes of the formula II via N-oxides of the formula III to halomethyloxazoles of the formula IV,

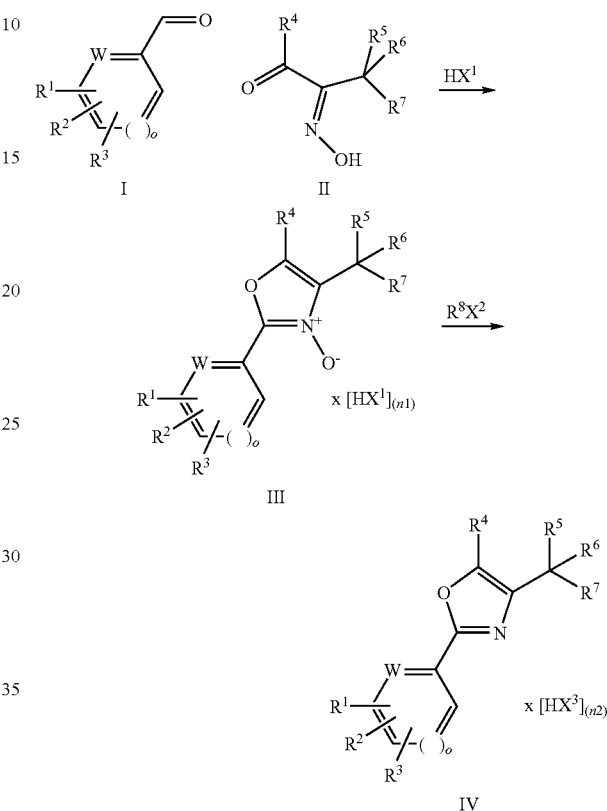

which comprises converting the aromatic aldehydes of the formula I using the α-ketoximes of the formula II

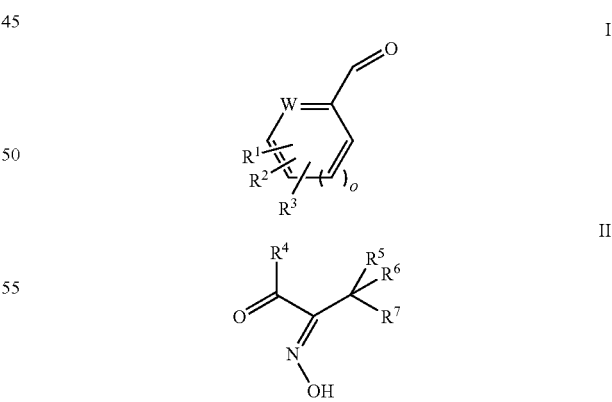

in which:
$R^1$ is H, (C1-C6)-alkyl, F, Cl, Br, I, O—(C0-C8)-alkylene-H, CF3, OCF3, SCF3, SF5, OCF2-CHF2, (C6-C10)-aryl, O—(C6-C10)-aryl, O—(C1-C4)-alkylene-(C6-C10)-aryl, NO2, $COOR^9$, $CONR^{10}R^{11}$, SH, or $NR^{10}R^{11}$, where aryl is unsubstituted or mono-, di- or trisubstituted by F, Cl, Br, I, (C1-C4)-alkyl, O—(C1-C4)-alkyl or $CF_3$;

where
- $R^9$ is H, Li, Na, K, ½Mg, ½Ca, ammonium ions which are unsubstituted or mono-, di- or trisubstituted by (C1-C4)-alkyl, or is (C1-C8)-alkyl,
- $R^{10}$ and $R^{11}$ are each independently H, $(C_1-C_5)$-alkyl, phenyl or $CH_2$-phenyl, where phenyl is unsubstituted or mono-, di- or trisubstituted by F, Cl, Br, I, (C1-C4)-alkyl, O—(C1-C4)-alkyl or $CF_3$;
- or
- $R^{10}$ and $R^{11}$ together are (C4-C5)-alkylene, in which one $CH_2$ group may be replaced by O, S, NH, N—$CH_3$ or N-benzyl;
- $R^2$ is H, (C1-C6)-alkyl, F, Cl, Br, I, O—(C0-C8)-alkylene-H, CF3, OCF3, SCF3, SF5, OCF2-CHF2, (C6-C10)-aryl, O—(C6-C10)-aryl, O—(C1-C4)-alkylene-(C6-C10)-aryl, NO2, $COOR^9$, $CONR^{10}R^{11}$, SH, or $NR^{10}R^{11}$, where aryl is unsubstituted or mono-, di- or trisubstituted by F, Cl, Br, I, (C1-C4)-alkyl, O—(C1-C4)-alkyl or $CF_3$;
  where $R^9$, $R^{10}$ and $R^{11}$ are each as defined above;
- $R^3$ is H, (C1-C6)-alkyl, F, Cl, Br, I, O—(C0-C8)-alkylene-H, CF3, OCF3, SCF3, SF5, OCF2-CHF2, (C6-C10)-aryl, O—(C6-C10)-aryl, O—(C1-C4)-alkylene-(C6-C10)-aryl, NO2, $COOR^9$, $CONR^{10}R^{11}$, SH, or $NR^{10}R^{11}$, where aryl is unsubstituted or mono-, di- or trisubstituted by F, Cl, Br, I, (C1-C4)-alkyl, O—(C1-C4)-alkyl or $CF_3$;

where $R^9$, $R^{10}$ and $R^{11}$ are each as defined above;
W is CH, N, if o=1;
W is O, S, NR12, if o=0;
o is 0 or 1;
R12 is H, (C1-C6)-alkyl, (C1-C6)-alkylenephenyl, phenyl;
$R^4$ is H, (C1-C8)-alkyl, (C3-C8)-cycloalkyl, (C1-C3)-alkylene-(C3-C8)-cycloalkyl, phenyl, (C1-C3)-alkylenephenyl, (C5-C6)-heteroaryl, (C1-C3)-alkylene-(C5-C6)-heteroaryl or (C1-C3)-alkyl which is fully or partly substituted by F, or $COOR^9$, CONR(10)R(11);
where $R^9$, $R^{10}$ and $R^{11}$ are each as defined above;
$R^5$ and $R^6$ are each independently
- H, (C1-C8)-alkyl, F, Cl, Br, I, O—(C0-C8)-alkylene-H, O—(C6-C10)-aryl, O—(C1-C4)-alkylene-(C6-C10)-aryl, $COOR^9$, $CONR^{10}R^{11}$, SH or $NR^{10}R^{11}$, where $R^9$, $R^{10}$, $R^{11}$ are as defined above;
or
$R^5$ and $R^6$ together
- are (C4-C5)-alkylene, in which one $CH_2$ group may be replaced by O, S, NH, N—$CH_3$ or N-benzyl;

$R^7$ is H or (C1-C8)-alkyl;

in the presence of acids $HX^1$, for example HCl, HBr, $H_2SO_4$, $H_3PO_4$, $HOOCCF_3$, $HOOCCCl_3$, $HO_3SCF_3$, $HO_3SCH_3$, $HO_3SC_6H_5$, $HO_3S-C_6H_4$-p-$CH_3$, HOOCH, to the N-oxides of the formula III

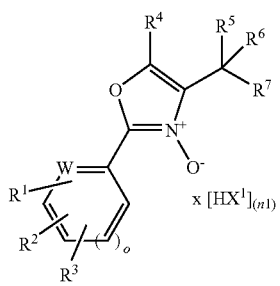

in which $R^1$, $R^3$, $R^4$, $R^5$, $R^6$, $R^7$ and $X^1$ are each as defined above and
n1 is 0, 1, ½ or ⅓;

and the latter is subsequently reacted
with the reagent $R^8X^2$ which means:
SOCl—Cl, SOBr—Br, $CH_3SO_2$—Cl, $CF_3SO_2$—CL, $C_6H_5SO_2$—Cl, p-$CH_3$—$C_6H_4$—$SO_2$—Cl, $CH_3SO_2$—$O_3SCH_3$, $CF_3SO_2$—$O_3SCF_3$, $C_6H_5SO_2$—$O_3SC_6H_5$ or p-$CH_3$—$C_6H_4$—$SO_2$—$O_3S$—$C_6H_4$-p-$CH_3$,
to give the halomethyloxazoles of the formula IV

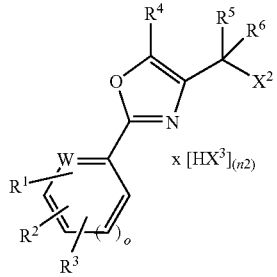

in which $R^1$, $R^2$, $R^3$, $R^4$, $R^5$, $R^6$ and $X^2$ are each as defined above and
X3 is Cl, Br, $CH_3SO_3$, $CF_3SO_3$, $C_6H_5SO_3$ or p-$CH_3$—$C_6H_4$—$SO_3$ and
n2 is 0 or 1.

DETAILED DESCRIPTION OF THE INVENTION

The invention preferably relates to a process for preparing the compounds of the formula IV in which:
W=CH and
o=1.

The invention preferably further relates to a process for preparing the compounds of the formula IV in which:
R1 is H;
$R^2$ is H, (C1-C6)-alkyl, F, Cl, Br, I, O—(C0-C8)-alkylene-H, CF3, OCF3, SCF3, SF5, OCF2-CHF2, (C6-C10)-aryl, O—(C6-C10)-aryl, O—(C1-C4)-alkylene-(C6-C10)-aryl, NO2, $COOR^9$, $CONR^{10}R^{11}$, SH, or $NR^{10}R^{11}$, where aryl is unsubstituted or mono-, di- or trisubstituted by F, Cl, Br, I, (C1-C4)-alkyl, O—(C1-C4)-alkyl or $CF_3$;
where
- $R^9$ is H, Li, Na, K, ½Mg, ½Ca, ammonium ions which are unsubstituted or mono-, di- or trisubstituted by (C1-C4)-alkyl, or is (C1-C8)-alkyl,
- $R^{10}$ and $R^{11}$ are each independently H, (C1-C5)-alkyl, phenyl or $CH_2$-phenyl,
  where phenyl is unsubstituted or mono-, di- or trisubstituted by F, Cl, Br, I, (C1-C4)-alkyl, O—(C1-C4)-alkyl or $CF_3$;
- or
- $R^{10}$ and $R^{11}$ together are (C4-C5)-alkylene, in which one $CH_2$ group may be replaced by O, S, NH, N—$CH_3$ or N-benzyl;

$R^3$ is H, (C1-C6)-alkyl, F, Cl, Br, I, O—(C0-C8)-alkylene-H, CF3, OCF3, SCF3, SF5, OCF2-CHF2, (C6-C10)-aryl, O—(C6-C10)-aryl, O—(C1-C4)-alkylene-(C6-C10)-aryl, NO2, $COOR^9$, $CONR^{10}R^{11}$, SH, or $NR^{10}R^{11}$, where aryl is unsubstituted or mono-, di- or trisubstituted by F, Cl, Br, I, (C1-C4)-alkyl, O—(C1-C4)-alkyl or $CF_3$;

where $R^9$, $R^{10}$ and $R^{11}$ are each as defined above.

The invention more preferably relates to a process for preparing the compounds of the formula IV in which:
R1 is H;
R² is H;
R³ is H, (C1-C6)-alkyl, F, Cl, Br, I, O—(C0-C8)-alkylene-H, CF3, OCF3, SCF3, SF5, OCF2-CHF2, (C6-C10)-aryl, O—(C6-C10)-aryl, O—(C1-C4)-alkylene-(C6-C10)-aryl, NO2, COOR$^9$, CONR$^{10}$R$^{11}$, SH, or NR$^{10}$R$^{11}$, where aryl is unsubstituted or mono-, di- or trisubstituted by F, Cl, Br, I, (C1-C4)-alkyl, O—(C1-C4)-alkyl or CF$_3$;
where
R$^9$ is H, Li, Na, K, ½Mg, ½Ca, ammonium ions which are unsubstituted or mono-, di- or trisubstituted by (C1-C4)-alkyl, or is (C1-C8)-alkyl,
R$^{10}$ and R$^{11}$ are each independently H, (C1-C5)-alkyl, phenyl or CH$_2$-phenyl,
where phenyl is unsubstituted or mono-, di- or trisubstituted by F, Cl, Br, I, (C1-C4)-alkyl, O—(C1-C4)-alkyl or CF$_3$;
or
R$^{10}$ and R$^{11}$ together are (C4-C5)-alkylene, in which one CH$_2$ group may be replaced by O, S, NH, N—CH$_3$ or N-benzyl.

The invention more preferably further relates to a process for preparing the compounds of the formula IV, in which:
R$^1$, R$^2$, R$^3$ are each independently H, (C1-C6)-alkyl, F, Cl, Br, I, O—(C0-C8)-alkylene-H, CF3, OCF3, OCF2-CHF2, (C6-C10)-aryl, O—(C6-C10)-aryl, O—(C1-C4)-alkylene-(C6-C10)-aryl, NO2, COOR$^9$, CONR$^{10}$R$^{11}$, SH, or NR$^{10}$R$^{11}$, where aryl is unsubstituted or mono-, di- or trisubstituted by F, Cl, Br, I, (C1-C4)-alkyl, O—(C1-C4)-alkyl or CF$_3$;
where
R$^9$ is H, Li, Na, K, ½Mg, ½Ca, ammonium ions which are unsubstituted or mono-, di- or trisubstituted by (C1-C4)-alkyl, or is (C1-C8)-alkyl,
R$^{10}$ and R$^{11}$ are each independently H, (C1-C5)-alkyl, phenyl or CH$_2$-phenyl,
where phenyl is unsubstituted or mono-, di- or trisubstituted by F, Cl, Br, I, (C1-C4)-alkyl, O—(C1-C4)-alkyl or CF$_3$;
or
R$^{10}$ and R$^{11}$ together are (C4-C5)-alkylene, in which one CH$_2$ group may be replaced by O, S, NH, N—CH$_3$ or N-benzyl.

The invention more preferably also relates to a process for preparing the compounds of the formula IV in which:
W=CH;
o=1;
R$^1$=H;
R$^2$=H, CH$_3$, OCH$_3$, Br or Cl;
R$^3$=H, CH$_3$, OCH$_3$, Br or Cl;
R$^4$=CH$_3$, CH$_2$CH$_3$ or CH(CH$_3$)$_2$;
R$^5$=H, CH$_3$, CH$_2$CH$_3$ or CH(CH$_3$)$_2$;
R$^6$=H, CH$_3$, CH$_2$CH$_3$ or CH(CH$_3$)$_2$;
X$^3$=Cl, CH$_3$SO$_3$ or p-CH$_3$—C$_6$H$_4$—SO$_3$ and
n2=0 or 1.

The unsubstituted or substituted ammonium ions in the definition of R$^9$ are preferably each triethylammonium.

In particular, the invention relates to a process for preparing compounds of the formula VIII,

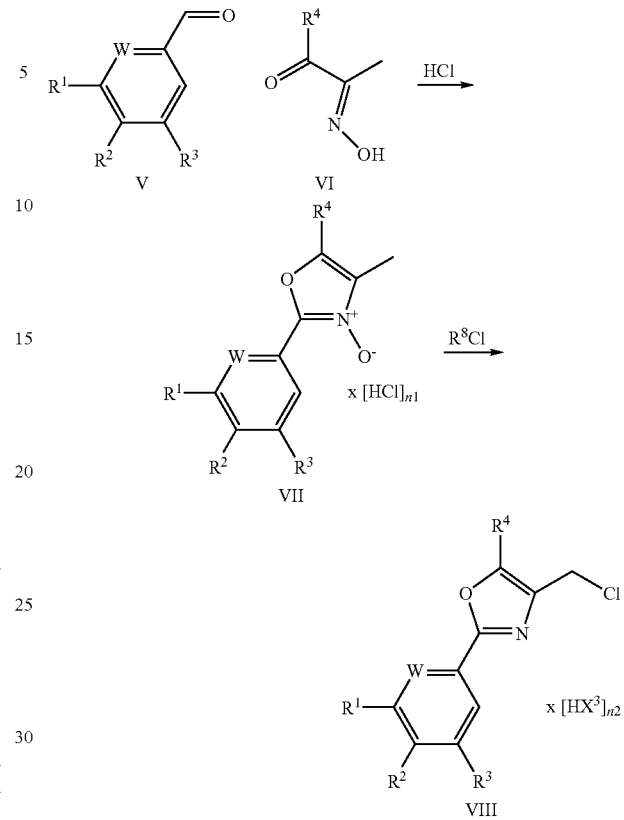

in which
R$^1$=H,
R$^2$=H or CH$_3$,
R$^3$=H or OCH$_3$,
R$^4$=CH$_3$ or CH(CH$_3$)$_2$,
W=CH,
X$^3$=Cl or CH$_3$SO$_3$ and
n2=0 or 1.

The invention most preferably relates to a process in which the reagent R$^8$X$^2$ has the structure:

SOCl—Cl, SOBr—Br, CH$_3$SO$_2$—Cl or p-CH$_3$—C$_6$H$_4$—SO$_2$—Cl.

In particular, the invention relates to a process in which the reagent R$^8$X$^2$ has either the structure SOCl—Cl (formula IX) or CH$_3$SO$_2$—Cl (formula X).

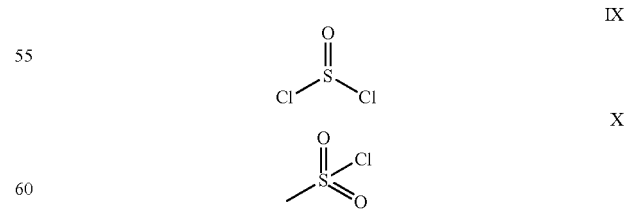

The N-oxide (formula III) may either be isolated or reacted further directly in solution.

When the N-oxide (formula III) or the oxazole (formula IV) is obtained as the salt (n1 ≠0 or n2 ≠0), it can be converted to the corresponding free base by treatment with a base such as aqueous solutions of sodium hydroxide, potassium hydroxide, sodium carbonate, potassium carbonate, sodium hydrogencarbonate and potassium hydrogencarbonate, for example.

For the reaction to form the N-oxides (formula I+formula II→formula III), useful reagents $HX^1$ are hydrogen halides, sulfuric acid and its acidic salt, phosphoric acid and its acidic salts, trifluoroacetic acid, trichloroacetic acid, trifluoromethanesulfonic acid, methanesulfonic acid, benzenesulfonic acid, p-toluenesulfonic acid, formic acid and also $HMSO_4$, $H_2MPO_4$, $HM_2PO_4$ where M=Na, K, preference being given to hydrogen halides. In a particularly preferred embodiment, hydrogen chloride will be selected. In the case of sulfuric acid, hydrogensulfates (n1=1) or sulfates (n1=½) can form; in the case of phosphoric acid, dihydrogenphosphates (n1=1), hydrogenphosphates (n1=½) or phosphates (n1=⅓) can form.

The reagent $HX^1$ can be used in stoichiometric amounts, based on the α-ketoxime (formula II), up to a high excess. A preferred working range is the use of stoichiometric amounts up to a 7-fold excess. Particular preference is given to a 1-6-fold excess.

For the reaction to form the N-oxides (formula I+formula II→formula III), the solvents used may be protic polar solvents such as carboxylic acids, aprotic dipolar solvents such as sulfoxides, nitriles or ethers or polyethers, aprotic polar solvents such as halogenated aromatic and aliphatic hydrocarbons, or aprotic nonpolar solvents such as aromatic and aliphatic hydrocarbons, or a mixture of the solvent groups. For example, useful solvents are formic acid, glacial acetic acid, propionic acid, N,N-dimethylformamide, N,N-dimethylacetamide, N-methylpyrrolidone, dimethyl sulfoxide, tetrahydrofuran, diethyl ether, diisopropyl ether, tert-butyl methyl ether, ethylene glycol dimethyl ether and higher homologs or dichloromethane and chlorobenzene or toluene, cyclohexane and n-heptane, in each case alone or in a mixture. In a preferred form, the reaction is carried out in glacial acetic acid, in a mixture of glacial acetic acid and ethylene glycol dimethyl ether, or in a mixture of glacial acetic acid and toluene.

The reaction temperatures for the formation of the N-oxides (formula I+formula II→formula III) can be varied within a wide range and depend upon factors including the solubility properties of the aldehydes (formula I) and α-ketoximes (formula II) to be converted. Thus, in principle, reaction temperatures of from minus 20° C. to 150° C. are possible, preference being given in general to reaction temperatures of from minus 10° C. to 90° C. In a particularly preferred embodiment, reaction temperatures of from 0° C. to 60° C. will be selected.

The formation of the N-oxides (formula I+formula II→formula III) can be carried out either in a closed system under elevated pressure or else in an open system under standard pressure, i.e., for example, by introducing a hydrogen halide gas into the system open to the atmosphere or by using a hydrogen halide gas in an organic solvent.

When a further function such as $COOR^9$ which can react with activated acid derivatives is present among the $R^1$ to $R^6$ radicals, the product can be obtained as the acid derivative $COX^2$ or, after preceding hydrolysis by processes known in principle, as the free acid COOH by acidic or alkaline hydrolysis.

The reagent $R^8X^2$ may be used in stoichiometric amounts, based on the intermediate N-oxide (formula III), up to a high excess. A preferred working range is the use of stoichiometric amounts up to a 5-fold excess. Particular preference is given to a 1-4-fold excess. This introduces the $X^2$ moiety (of $R^8X^2$) in formula IV in covalently bonded form and converts $R^8$ to $HX^3$ by hydrolysis.

For the reaction for the formation of the halomethyloxazoles (formula III→formula IV), the solvents used may be aprotic dipolar solvents such as amides, sulfoxides, nitriles or ethers or polyethers, aprotic polar solvents such as halogenated aromatic and aliphatic hydrocarbons, or aprotic nonpolar solvents such as aromatic and aliphatic hydrocarbons, or a mixture of the solvent groups. For example, useful solvents are N,N-dimethylformamide, N,N-dimethylacetamide, N-methylpyrrolidone, dimethyl sulfoxide, tetrahydrofuran, diethyl ether, diisopropyl ether, tert-butyl methyl ether, ethylene glycol dimethyl ether and higher homologs, or dichloromethane and chlorobenzene or toluene, cyclohexane and n-heptane, in each case alone or in a mixture. In a preferred form, the reaction is carried out in dichloromethane or toluene. The reaction may also be carried out without solvent in an excess of the thionyl chloride or methanesulfonyl chloride reagents.

The reaction temperatures for the formation of the halomethyloxazoles (formula III→formula IV) can be varied within a wide range and depend upon factors including the solubility properties for the aldehydes and α-ketoximes to be converted. Thus, in principle, reaction temperatures from minus 20° C. to 150° C. are possible, preference being given generally to reaction temperatures of from 20° C. to 120° C. In a particularly preferred embodiment, reaction temperatures of from 20° C. to 80° C. will be selected.

Halogen represents fluorine, chlorine, bromine or iodine, preferably fluorine, chlorine, bromine, more preferably chlorine or bromine, and most preferably chlorine.

An alkyl radical is understood to mean a straight-chain or branched hydrocarbon chain having from one to six carbons, for example methyl, ethyl, propyl, butyl, pentyl, hexyl, isopropyl, isobutyl, neopentyl, tert-butyl.

The alkyl radicals may be mono-, di- or trisubstituted by suitable groups, for example: F, Cl, Br, I, CF3, NO2, N3, CN, COOH, COO(C1-C6)-alkyl, CONH2, CONH(C1-C6)-alkyl, CON[(C1-C6)-alkyl]2, (C3-C8)-cycloalkyl, (C2-C6)-alkenyl, (C2-C6)-alkynyl, (C6-C10)-aryl.

An aryl radical is understood to mean a phenyl, naphthyl, biphenyl, tetrahydronaphthyl, alpha- or beta-tetralonyl, indanyl or indan-1-onyl radical. The aryl radicals may be mono-, di- or trisubstituted by suitable groups, for example: F, Cl, Br, I, CF3, NO2, SF5, N3, CN, COOH, COO(C1-C6)-alkyl, CONH2, CONH(C1-C6)-alkyl, CON[(C1-C6)alkyl]2, (C3-C8)-cycloalkyl, (C1-C10)-alkyl, (C2-C6)-alkenyl, (C2-C6)-alkynyl, O—(C1-C6)-alkyl, O—CO—(C1-C6)-alkyl, O—CO—(C6-C10)-aryl.

A cycloalkyl radical is understood to mean a three- to eight-membered ring system which contains one or more rings and is present in saturated or partially unsaturated (with one or two double bonds) form which is composed exclusively of carbon atoms, for example cyclopropyl, cyclopentyl, cyclopentenyl, cyclohexyl or adamantyl. The cycloalkyl radicals may be mono-, di- or trisubstituted by suitable groups, for example: F, Cl, Br, I, CF3, NO2, N3, CN, COOH, COO(C1-C6)-alkyl, CONH2, CONH(C1-C6)-alkyl, CON[(C1-C6)alkyl]2, (C3-C8)-cycloalkyl, (C1-C10)-alkyl, (C2-C6)-alkenyl, (C2-C6)-alkynyl, O—(C1-C6)-alkyl, O—CO—(C1-C6)-alkyl, O—CO—(C6-C10)-aryl.

A heteroaryl radical is understood to mean a C5-C6-heterocycle which may contain from 1 to 4 heteroatoms from the group O, N, S. Examples include furan, thiophene, pyrrole, pyridine, pyrazine, pyrimidine, pyridazine, oxazole, isoxazole, thiazole, isothiazole, furazan, tetrazole.

The inventive compounds of the formula IV can be reacted, for example, according to DE 102004040736.3 further to give pharmaceutically active substances, the PPAR agonists.

EXAMPLES

Example 1

2-(3-Methoxyphenyl)-4,5-dimethyloxazole 3-oxide (formula XI)

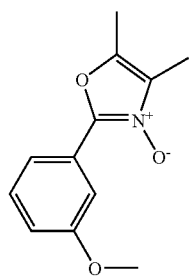

XI 15.2 g (0.150 mol) of 2,3-butanedione monoxime were initially charged and 260 ml of toluene, 22.1 g (0.157 mol) of 3-methoxybenzaldehyde and 70 ml (73.4 g, 1.224 mol) of glacial acetic acid were added with stirring. 27.3 g (0.749 mol) of hydrogen chloride gas were introduced with cooling at such a rate that the internal temperature was <22° C. Subsequently, the mixture was stirred for up to 16 h. With stirring, the reaction mixture was added to 600 ml of water (exothermic reaction). The pH was adjusted to 10.6, for which 172 ml (1.930 mol) of 33% aqueous sodium hydroxide solution were required; the internal temperature was kept <32° C. by external cooling. Two phases formed and were separated. The aqueous phase was extracted twice with 100 ml each time of toluene and subsequently discarded. The combined organic phases were concentrated under reduced pressure while distilling off 50 ml. The thus obtained toluenic solution (420 ml) was used directly for the synthesis of 4-chloromethyl-2-(3-methoxyphenyl)-5-methyloxazole hydrochloride.

Yield: 32.9 g (100%) of 2-(3-methoxyphenyl)-4,5-dimethyloxazole 3-oxide, not isolated, assumption for the calculation of the subsequent stage.

The data which follow were measured on the pure substance which was obtained after the solvent of the organic phases had been distilled off completely.

Melting point: 114° C.

$^1$H NMR (CDCl$_3$, 400 MHz) δ (ppm)=2.20 (s, 3H); 2.35 (s, 3H); 3.87 (s, 3H); 6.98 (m, 1H); 7.38 (m, 1H); 7.88 (m, 3H); 8.26 (m, 1H).

Example 2

4-Chloromethyl-2-(3-methoxyphenyl)-5-methyloxazole hydrochloride (formula XII)

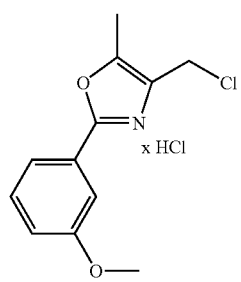

XII

The entire toluenic solution from Example 1 (420 ml) was admixed at 60° C. dropwise with 54.2 g (0.456 mol) of thionyl chloride and stirred at <60° C. for up to 22 h. Subsequently, the mixture was concentrated by distilling off 229 ml. The suspension was cooled to <20° C., and the product was isolated by filtration with suction, washed 3 times with 20 ml each time of toluene and dried at elevated temperature under reduced pressure.

Yield: 23.2 g (56%) of 4-chloromethyl-2-(3-methoxyphenyl)-5-methyloxazole hydrochloride Melting point: 117° C.

$^1$H NMR (CDCl$_3$, 400 MHz) δ (ppm)=2.58 (s, 3H); 3.92 (s, 3H); 4.78 (s, 2H); 7.15 (m, 1H); 7.42 (m, 1H); 7.79 (m, 1H); 8.04 (m, 1H).

Example 3

4-Chloromethyl-2-(3-methoxyphenyl)-5-methyloxazole (formula XIII)

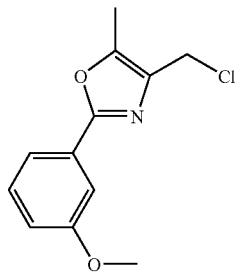

XIII 10.1 g (0.037 mol) of 4-chloromethyl-2-(3-methoxyphenyl)-5-methyloxazole hydrochloride were suspended in 100 ml of water and 75 ml of dichloromethane. With stirring, a pH of 12 was established in the water phase with 45 ml (0.023 mol) of aqueous sodium hydroxide solution. Subsequently, the phases were separated and the aqueous phase was discarded. The organic phase was concentrated by distillation completely under reduced pressure. The remaining oil crystallized through after the addition of seed crystals.

Yield: 8.0 g (92%) of 4-chloromethyl-2-(3-methoxyphenyl)-5-methyloxazole

Melting point: 46-50° C.

$^1$H NMR (CDCl$_3$, 400 MHz) δ (ppm)=2.43 (s, 3H); 3.88 (s, 3H); 4.56 (s, 2H); 6.99 (m, 1H); 7.35 (m, 1H); 7.54 (m, 1H); 7.60 (m, 1H).

Example 4

4,5-Dimethyl-2-p-tolyloxazole 3-oxide hydrochloride (formula XIV)

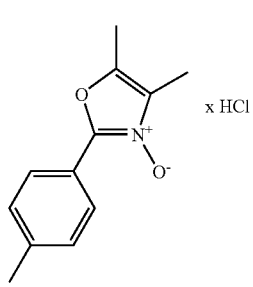

XIV 100 g (979 mmol) of butane-2,3-dione monoxime were initially charged and dissolved in 500 ml of acetic acid. 120 g (979 mmol) of 4-methylbenzaldehyde were added. 100 g (2.74 mol) of hydrogen chloride gas were introduced at such a rate that an internal temperature of 40° C. was not exceeded. Subsequently, the mixture was stirred at 35-40° C. for a further 2-3 hours. With intensive cooling, 2 l of tert-butyl methyl ether were added. The reaction mixture was stirred at 10° C. for 1 hour. The product was isolated by filtration with suction, washed with tert-butyl methyl ether and dried at elevated temperature under reduced pressure.

Yield: 213 g (91%) of 4,5-dimethyl-2-p-tolyloxazole 3-oxide hydrochloride

Melting point: 101° C.

$^1$H NMR (DMSO-D$_6$, 500 MHz) δ (ppm)=10.30 (s$_{br}$, 1H), 8.17 (d, J=8.3 Hz; 2H), 7.47 (d, J=8.3 Hz; 2H), 2.44 (s, 3H), 2.42 (s, 3H)

Example 5

4-Chloromethyl-5-methyl-2-p-tolyloxazole (formula XV)

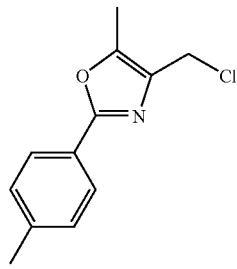

XV 32.8 g (137 mmol) of 4,5-dimethyl-2-p-tolyloxazole 3-oxide hydrochloride were suspended in 165 ml of dichloromethane. 17.5 g (151 mmol) of methanesulfonyl chloride were added. The reaction was stirred at reflux up to full conversion (HPLC). Subsequently, 200 ml of ethylene glycol dimethyl ether were added, and the dichloromethane was distilled off under reduced pressure. The reaction mixture was cooled to 15° C. and 250 ml of water were added. The mixture was stirred at 15° C. for 1 hour. The precipitated product was isolated by filtration with suction, washed with water and dried at elevated temperature under reduced pressure.

Yield: 27.6 g (91%) of 4-chloromethyl-5-methyl-2-p-tolyloxazole

Melting point: 95° C.

$^1$H NMR (DMSO-D$_6$, 500 MHz) δ (ppm)=7.82 (d, J=8.1 Hz, 2H), 7.33 (d, J=8.1 Hz, 2H), 4.74 (s, 2H), 2.43 (s, 3H), 2.37 (s, 3H)

Example 6

4-Methylpentane-2,3-dione 2-oxime (formula XVI)

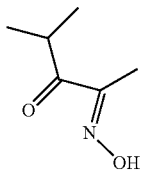

XVI 100 g (948 mmol) of 2-methylpentan-3-one were dissolved in 400 ml of tert-butyl methyl ether. 50 g (274 mmol) of solution of hydrochloride in ethylene glycol dimethyl ether (20%) were added. Subsequently, a solution of 117 g (949 mmol) isoamyl nitrite in 150 ml of tert-butyl methyl ether was added dropwise within 60 minutes. The solvent was removed fully under reduced pressure. The residue was taken up in 300 ml of n-heptane and concentrated again under reduced pressure. After 200 ml of n-heptane had been added, extraction was effected with 522 ml of sodium hydroxide solution (2 molar). After phase separation, the aqueous phase was washed with n-heptane. The aqueous phase was acidified by adding conc. hydrochloric acid. The product was isolated by filtration with suction, washed with water and dried at elevated temperature under reduced pressure.

Yield: 61.1 g (50%) of 4-methylpentane-2,3-dione 2-oxime

Melting point: 94° C.

$^1$H NMR (DMSO-D$_6$, 500 MHz) δ (ppm)=12.3 (s, 1H), 3.54 (sept, J=6.9 Hz, 1H), 1.82 (2, 3H), 1.02 (s, 3H), 1.01 (s, 3H).

Example 7

5-Isopropyl-2-(3-methoxyphenyl)-4-methyloxazole 3-oxide (formula XVII)

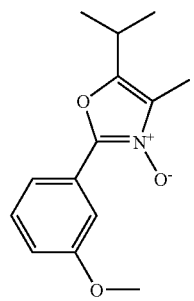

XVII 19.0 g (137 mmol) of 3-methoxybenzaldehyde were added to a solution of 18.0 g (137 mmol) of 4-methylpentane-2,3-dione 2-oxime in 30 g (99 mmol) of solution of hydrogen chloride in acetic acid (12%) and 30 g (164 mmol) of solution of hydrogen chloride in ethylene glycol dimethyl ether (20%). The reaction was stirred at 50-55° C. for 3 hours and at room temperature for 60 hours. Subsequently, 500 ml of water and 300 ml of tert-butyl methyl ether were added before a pH of 3-4 was established by adding sodium hydrogen carbonate. After phase separation, the aqueous phase was extracted twice with 100 ml each time of tert-butyl methyl ether. The combined organic phases were washed with 4×100 ml of water and concentrated fully under reduced pressure.

Yield: 42.8 g (79% purity) (100%) of 5-isopropyl-2-(3-methoxyphenyl)-4-methyloxazole 3-oxide $^1$H NMR (DMSO-D$_6$, 500 MHz) δ (ppm)=8.12 (m, 1H), 7.86 (d, J=8.0 Hz, 1H), 7.48 (t, J=8.0 Hz, 1H), 7.06 (dd, J=2.4, 8.0 Hz, 1H), 3.82 (s, 3H), 3.16 (sept, J=7.0 Hz, 1H), 2.12 (s, 3H), 1.29 (d, J=7.0 Hz, 3H).

Example 8

4-Chloromethyl-5-isopropyl-2-(3-methoxyphenyl) oxazole (formula XVIII)

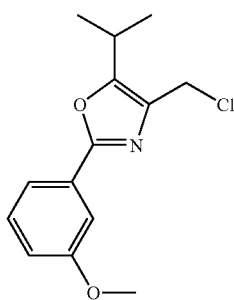

XVIII 75 g (648 mmol) of methanesulfonyl chloride were added at a temperature of 20° C. to a solution of 135 g (435 mmol) of 5-isopropyl-2-(3-methoxyphenyl)-4-methyloxazole 3-oxide in 500 ml of dichloromethane. The reaction was stirred at 40-45° C. up to full conversion. 500 ml of tert-butyl methyl ether and 300 ml of water were added. Addition of 20% sodium hydroxide solution established a pH of 8. After phase separation, the organic phase was washed with 3×200 ml of water. The organic phase was concentrated fully under reduced pressure.

Yield: 132 g (87% purity) (99%) of 4-chloromethyl-5-isopropyl-2-(3-methoxyphenyl)-oxazole $^1$H NMR (DMSO-D$_6$, 500 MHz) δ (ppm)=7.55 (m, 1H), 7.45 (m, 2H), 7.10 (ddd, J=0.9, 2.7, 5.6 Hz, 1H), 4.77 (s, 2H), 3.85 (s, 3H), 3.33 (sept, 7.0 Hz, 1H), 1.30 (d, J=7.0 Hz, 6H).

We claim:
1. A compound of formula III,

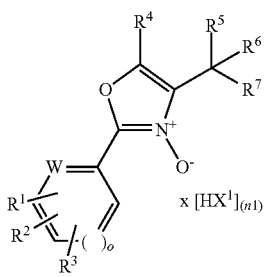

III wherein:
R$^1$, R$^2$ and R$^3$ are each independently H, (C1-C6)-alkyl, F, Cl, Br, I, O—(C0-C8)-alkylene-H, CF$_3$, OCF$_3$, SCF$_3$, SF$_5$, OCF$_2$—CHF$_2$, (C6-C10)-aryl, O—(C6-C10)-aryl, O—(C1-C4)-alkylene-(C6-C10)-aryl, NO$_2$, COOR$^9$, CONR$^{10}$R$^{11}$, SH, or NR$^{10}$R$^{11}$, wherein the aryl is un-substituted or mono-, di- or tri-substituted by F, Cl, Br, I, (C1-C4)-alkyl, O—(C1-C4)-alkyl or CF$_3$;
R$^9$ is H, (C1-C8)-alkyl, Li, Na, K, ½Mg, ½Ca, or an ammonium ion which is un-substituted or mono-, di- or tri-substituted by (C1-C4)-alkyl;
R$^{10}$ and R$^{11}$ are each independently H, (C1-C5)-alkyl, phenyl or CH$_2$-phenyl, wherein the phenyl is un-substituted or mono-, di- or tri-substituted by F, Cl, Br, I, (C1-C4)-alkyl, O—(C1-C4)-alkyl or CF$_3$, or R$^{10}$ and R$^{11}$ together are (C4-C5)-alkylene, wherein one CH$_2$ group may be replaced by O, S, NH, N—CH$_3$ or N-benzyl;
W is CH;
o is 1;
R12 is H, (C1-C6)-alkyl, (C1-C6)-alkylenephenyl, or phenyl;
R$^4$ is H, COOR$^9$, CONR(10)R(11), (C1-C8)-alkyl, (C3-C8)-cycloalkyl, (C1-C3-alkylene-(C3-C8)-cycloalkyl, phenyl, (C1-C3)-alkylenephenyl, (C5-C6)-heteroaryl, (C1-C3)-alkylene-(C5-C6)-heteroaryl, or (C1-C3)-alkyl, wherein the (C1-C3)-alkyl is fully or partly substituted by F;
R$^5$ and R$^6$ are each independently H, (C1-C8)-alkyl, F, Cl, Br, I, O—(C0-C8)-alkylene-H, O—(C6-C10)-aryl, O—(C1-C4)-alkylene-(C6-C10)-aryl, COOR$^9$, CONR$^{10}$R$^{11}$, SH or NR$^{10}$R$^{11}$, or
R$^5$ and R$^6$ together are (C4-C5)-alkylene, wherein one CH$_2$ group may be replaced by O, S, NH, N—CH$_3$ or N-benzyl;
R$^7$ is H;
n1 is 0, 1, ½ or ⅓; and
HX$^1$ is HCl, HBr, H$_2$SO$_4$, H$_3$PO$_4$, HOOCCF$_3$, HOOC-CCl$_3$, HO$_3$SCF$_3$, HO$_3$SCH$_3$, HO$_3$SC$_6$H$_5$, HO$_3$S—C$_6$H$_4$-p-CH$_3$, or HOOCH.

2. The compound according to claim 1, wherein:
R1 is H.

3. The compound according to claim 1 wherein:
R$^2$ is H.

4. The compound according to claim 1, wherein:
R$^1$, R$^2$ and R$^3$ are each independently H, (C1-C6)-alkyl, F, Cl, Br, I, O—(C0-C8)-alkylene-H, CF3, OCF3, OCF2-CHF2, (C6-C10)-aryl, O—(C6-C10)-aryl, O—(C1-C4)-alkylene-(C6-C10)-aryl, NO2, COOR$^9$, CONR$^{10}$R$^{11}$, SH, or NR$^{10}$R$^{11}$, wherein the aryl is unsubstituted or mono-, di- or trisubstituted by F, Cl, Br, I, (C1-C4)-alkyl, O—(C1-C4)-alkyl or CF$_3$.

5. The compound according to claim 1, wherein:
R$^1$ is H;
R$^2$ is H, CH$_3$, OCH$_3$, Br or Cl;
R$^3$ is H, CH$_3$, OCH$_3$, Br or Cl;
R$^4$ is CH$_3$, CH$_2$CH$_3$ or CH(CH$_3$)$_2$;
R$^5$ is H, CH$_3$, CH$_2$CH$_3$ or CH(CH$_3$)$_2$;
R$^6$ is H, CH$_3$, CH$_2$CH$_3$ or CH(CH$_3$)$_2$;
HX$^1$ is HCl, HO$_3$SCH$_3$ or HO$_3$S—C$_6$H$_4$-p-CH$_3$; and
n1 is 0 or 1.

6. The compound according to claim 1, of formula XI

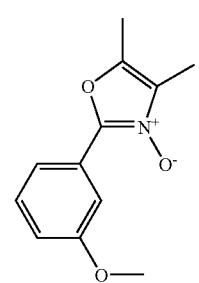

XI

7. The compound according to claim 1, of formula XIV
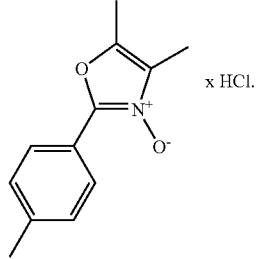
XIV
x HCl.
8. The compound according to claim 1, of formula XVII
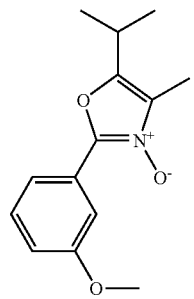
XVII
* * * * *